(12) United States Patent
Qian et al.

(10) Patent No.: US 11,549,225 B2
(45) Date of Patent: Jan. 10, 2023

(54) DEVICE FOR DETECTING COMPACTION AND SHEAR STRENGTH CHARACTERISTICS OF ASPHALT MIXTURE DURING CONSTRUCTION COMPACTION

(71) Applicant: Changsha University of Science and Technology, Changsha (CN)

(72) Inventors: Guoping Qian, Changsha (CN); Huanan Yu, Changsha (CN); Changyun Shi, Changsha (CN); Xiangbing Gong, Changsha (CN); Xi Li, Changsha (CN); Jun Cai, Changsha (CN); Wenchao Wu, Changsha (CN)

(73) Assignee: Changsha University of Science and Technology, Changsha (CN)

( * ) Notice: Subject to any disclaimer, the term of this patent is extended or adjusted under 35 U.S.C. 154(b) by 340 days.

(21) Appl. No.: 16/861,975

(22) Filed: Apr. 29, 2020

(65) Prior Publication Data
US 2021/0087759 A1     Mar. 25, 2021

(30) Foreign Application Priority Data

Sep. 19, 2019 (CN) .......................... 201910884498.5

(51) Int. Cl.
*G01N 33/00* (2006.01)
*E01C 23/01* (2006.01)
*G01N 33/42* (2006.01)

(52) U.S. Cl.
CPC ............. *E01C 23/01* (2013.01); *G01N 33/42* (2013.01); *G01N 2203/0003* (2013.01); *G01N 2203/0021* (2013.01)

(58) Field of Classification Search
CPC .................... E01C 23/01; G01N 33/42; G01N 2203/0003; G01N 2203/0021
See application file for complete search history.

(56) References Cited

U.S. PATENT DOCUMENTS

| | | | | |
|---|---|---|---|---|
| 5,365,793 | A | * | 11/1994 | Terrel ..................... G01N 33/42 73/813 |
| 5,942,679 | A | * | 8/1999 | Sandstrom ............ E01C 19/288 404/133.05 |

(Continued)

OTHER PUBLICATIONS

Goodman, Stephen N. et al., Shear Properties as Viable Measures for Characterization of Permanent Deformation of Asphalt Concrete Mixtures, Canadian Strategic Highway Research Program, 1994, pp. 154-161, Transportation Research Record 1789, Paper No. 02-3835, Department of Civil Environmental Engineering, Carleton University, Canada.

(Continued)

*Primary Examiner* — Max H Noori
(74) *Attorney, Agent, or Firm* — Howard & Howard Attorneys LLC

(57) ABSTRACT

A device is for detecting compaction and shear strength characteristics of an asphalt mixture during construction compaction. The device includes a fixed frame and a detection system. The detection system includes a display, a control panel, a test claw, an electric motor, a lift switch, a torque sensor and a temperature sensor. The control panel includes a power switch for controlling the electric motor and a speed regulator for controlling a rotation speed of the test claw. An output end of the electric motor is connected to an input end of the torque sensor, and an output end of the torque sensor is connected to an input end of the test claw. An output end of the test claw is provided with a claw-shaped blade. The claw-shaped blade is provided therein with the temperature sensor.

9 Claims, 2 Drawing Sheets

(56) References Cited

U.S. PATENT DOCUMENTS

| | | | | |
|---|---|---|---|---|
| 5,952,561 | A * | 9/1999 | Jaselskis | G01N 33/42 73/78 |
| 6,609,407 | B1 * | 8/2003 | Tambini | G01L 25/003 73/1.09 |
| 7,047,820 | B2 * | 5/2006 | Bahia | G01N 3/565 73/819 |
| 11,339,540 | B1 * | 5/2022 | Cobb | E01C 19/45 |
| 2010/0005898 | A1 * | 1/2010 | Regimand | G01N 33/42 73/803 |
| 2013/0290062 | A1 * | 10/2013 | Patel | G06Q 10/06313 705/7.23 |
| 2015/0167257 | A1 * | 6/2015 | Korb | E01C 7/36 404/76 |
| 2019/0003134 | A1 * | 1/2019 | Andersson | G01N 33/42 |
| 2019/0033189 | A1 * | 1/2019 | Coe | G01N 3/56 |
| 2019/0078270 | A1 * | 3/2019 | Laugwitz | E01C 19/288 |
| 2021/0088430 | A1 * | 3/2021 | Qian | G01N 3/24 |
| 2022/0024324 | A1 * | 1/2022 | Sopko, Jr. | B60L 50/51 |
| 2022/0090953 | A1 * | 3/2022 | Perko | G01F 23/14 |
| 2022/0136184 | A1 * | 5/2022 | Mühlhausen | E01C 19/288 404/122 |

OTHER PUBLICATIONS

Gudimettla, Jagan M. et al., Workability of Hot-Mix Asphalt, Transportation Research Record: Journal of the Transportation Research Board, 2004, pp. 229-237, No. 1891, Washington, D.C., U.S.A.

Hangqi, Shi et al., Evaluation of Asphalt Mixture Compaction Workability Based on Shear Compactor, 217, 71 pages.

Wen, Tang et al., Shear Resistance Performance of Asphalt Mixtures at Different Temperature and Its Evaluation Indexes, China Academic Journal Electronic Publishing House, Mar. 3, 2012, pp. 191-195, No. 3, CCCC Second Highway Consultants Co., Ltd., Wuhan, China.

Zheng-Qi, Zhang et al., Study on Factors Effecting on Compaction Property of Asphalt Mixture, Journal of Wuhan University of Technology, Jun. 2012, pp. 36-41, vol. 34, No. 6, China Academic Journal Electronic Publishing House, Wuhan, China.

* cited by examiner

DEVICE FOR DETECTING COMPACTION AND SHEAR STRENGTH CHARACTERISTICS OF ASPHALT MIXTURE DURING CONSTRUCTION COMPACTION

CROSS-REFERENCE TO RELATED APPLICATION(S)

The present application claims priority to and the benefit of Chinese Patent Application No. 201910884498.5, filed Sep. 19, 2019, the entire disclosure of which is hereby expressly incorporated by reference.

TECHNICAL FIELD

The present invention belongs to the technical field of asphalt mixture compaction detection, and relates to a device for detecting compaction and shear strength characteristics of an asphalt mixture during construction compaction. The detection device is used to evaluate the compaction quality of the asphalt mixture, and to monitor and guide the construction quality and construction process accordingly based on real-time detection results.

BACKGROUND

Compaction is the last step in the formation of asphalt pavement. Construction compaction control is a necessary method to ensure that the quality, physical and mechanical properties and pavement performance of asphalt mixture meet requirements. China's technical specifications for asphalt pavement construction specify the compaction control method of asphalt pavement, as well as detection location, frequency and allowable deviation, etc. Traditional compaction detection methods include sand filling method, water bag method, cutting ring method, wax seal method and nuclear density gage method, etc.

However, these construction control methods are mainly used for detection in a construction acceptance stage. The detection is post-construction detection, lagging behind the compaction process. Therefore, over- and under-compaction sections cannot be found in time. The combination of compaction machinery and compaction times at the construction site are generally determined by experience. It is impossible to adjust and control the construction process and construction quality according to detection results. Due to the lack of proper asphalt mixture compaction status detection devices and methods, there are difficulties in quality supervision and construction process control.

In 2002, Stephen N. Goodman and Yasser Hassan et al. proposed that shear strength was a feasible measure to characterize the permanent deformation of asphalt concrete. They used an in-situ shear stiffness test (InSiSST) facility developed by Carleton University to analyze the shear-strength-related characteristics of the mixture, including binder property, binder amount and aggregate characteristics (type, grading, etc.). However, this study is only applicable to post-construction detection of pavements after open traffic, and is difficult to apply to on-line construction detection.

In 2003, Jagan M. Gudimettla and L. Allen Cooley, Jr. et al. tested mixture workability test equipment and evaluated the workability of asphalt mixture by applying a torque to a crosshead inserted into the asphalt mixture before paving. The test results showed that different factors had largely different effects on the compactability of asphalt mixture. These factors included asphalt binder characteristics, mixture temperature, aggregate type and nominal maximum size of aggregate in a descending order of their effects. This equipment could only measure the torque of asphalt mixture. The study did not show a direct correlation between the workability and compaction of asphalt mixture, and is not suitable for compaction detection during the construction stage.

In 2005, China's professor Zhang Zhengqi used multiple groups of asphalt mixtures for laboratory gyratory compaction analysis. He proposed to use a compact energy index of a compaction curve from an initial compaction status to design compaction times to evaluate the compactability of asphalt pavement. However, due to a boundary problem, this study is difficult to determine the compaction energy of site construction, and cannot be directly used for construction guidance.

In 2012, Tang Wen and Sun Lijun et al. studied the changing shear strength of asphalt mixture at different temperatures. They found a good correlation between different shear evaluation indexes through different shear strength tests. Their study showed that temperature had a great influence on the shear strength of asphalt mixture and the temperature characteristics of asphalt mixture should be fully considered to evaluate the shear strength thereof.

In 2017, Xu Shifa and Shi Hangqi et al. from Beijing University of Civil Engineering and Architecture used a laboratory shear compactor to form an asphalt mixture. They further explored the compaction and shear strength characteristics of the mixture to obtain a corresponding workable compaction temperature under the use of the shear compactor. They proposed to use a compaction shear stress index to evaluate the compaction performance of the mixture and analyzed the feasibility of using shear strength to evaluate the compaction status of the mixture. However, due to the complexity of the equipment, this study is difficult to use for on-site mixture compaction detection.

Great progress have been made in the compaction detection of asphalt mixture at home and abroad. However, most of the current research still focuses on the post-construction compaction detection of asphalt mixture, and online detection has not been realized. Therefore, it is impossible to adjust and control the construction process and construction quality according to detection results. At present, there is a lack of a device for detecting the compaction status of the asphalt mixture during on-site construction compaction. Therefore, it is necessary to further research the real-time detection of compaction quality and research the evaluation indexes and standards of the asphalt mixture.

SUMMARY

In view of the shortcomings of the prior art, an objective of the present invention is to provide a device for detecting compaction and shear strength characteristics of an asphalt mixture during construction compaction. The device measures a compaction detection index of the asphalt mixture during compaction simply, quickly and accurately. The device is used to accurately evaluate a compaction effect of the asphalt mixture, determine a compaction status of the asphalt mixture during a construction process, and adjust and control the construction process and construction quality in time according to a detection result.

In order to achieve the above technical objective, the present invention provides a device for detecting compaction and shear strength characteristics of an asphalt mixture during construction compaction. The device includes a fixed frame and a detection system. The detection system includes a display, a control panel, a test claw, an electric motor for driving the test claw to rotate, a lift switch for controlling a vertical movement of the test claw, a torque sensor and a temperature sensor. The control panel includes a power switch for controlling the electric motor and a speed regulator for controlling a rotation speed of the test claw. An output end of the electric motor is connected to an input end of the torque sensor, and an output end of the torque sensor is connected to an input end of the test claw. An output end of the test claw is provided with a claw-shaped blade. The claw-shaped blade is provided therein with the temperature sensor.

Preferably, there are at least 3 claws of the claw-shaped blade, and more preferably 3-6.

Preferably, the bottom of the claw-shaped blade is a conical tip, which is convenient for pressing into the asphalt mixture with a certain degree of compaction.

Preferably, a universal wheel is arranged at the bottom of the fixed frame to facilitate a free movement.

The detection device of the present invention immediately detects the compaction status of a pavement with a certain degree of compaction on a construction site during a compaction process to obtain a compaction detection index $K/K_{min}$ of the asphalt mixture. The device compares the compaction detection index $K/K_{min}$ obtained in real time with a standard interval of $K/K_{min}$ in a standard table to determine the compaction status of the asphalt mixture, so as to adjust and control the construction process and construction quality in time. When a value of $K/K_{min}$ is greater than a right end value of the standard interval, a section is under-compacted and supplementary compaction construction should be implemented in time. When the value of $K/K_{min}$ is smaller than a left end value of the standard interval, the section is over-compacted and a remedial measure for over-compaction should be taken in time. When the value of $K/K_{min}$ is within the range of the standard interval, the compaction of the section is completed and a next stage of construction may be implemented. In an actual detection process, the blade of the test claw rotates relatively slow and the asphalt mixture has a certain self-healing property at a high temperature. Therefore, when the blade of the test claw is pressed into a constructed pavement for detection, it does not cause large damage to the pavement. The real-time detection data is instructive to a subsequent construction process, and can be used to prevent and remedy under- and over-compaction conditions to ensure a good compaction effect of the asphalt mixture.

The device for detecting compaction and shear strength characteristics of an asphalt mixture during construction compaction according to the present invention is specifically operated as follows:

step 1: surface, intermediate and base courses of the asphalt mixture are paved separately on site; after the base course is compacted by a compactor, the detection device is moved to a selected detection point, and the universal wheel is fixed;

step 2: the claw-shaped blade on the output end of the test claw is pressed into the asphalt mixture with a certain degree of compaction through a lift switch;

step 3: the power switch of the electric motor is turned on; the electric motor drives a stirring shaft to rotate slowly and uniformly with a speed freely selected between 5°/min and 10°/min; a temperature T (° C.) and a torque M (N·m) on the display are recorded;

step 4: the torque M obtained in step 3 is used to calculate a shear strength and a shear stiffness of the asphalt mixture:

$$F = G\gamma = \frac{M\rho}{I_p}$$

$$G = \frac{F}{\gamma} = \frac{M\rho}{\gamma I_p}$$

where, F is the shear strength, G is the shear stiffness, $\gamma$ is a shear strain, $\rho$ is a radius, and $I_p$ is a polar moment of inertia; and step 5: the shear strength and the shear stiffness obtained in step 4 are used to calculate a compaction detection index $K/K_{min}$ of the asphalt mixture, where K is defined as an inverse of the shear stiffness, $$K = \frac{1}{G},$$

and $K_{min}$ is a minimum value of K of the asphalt mixture under a corresponding degree of compaction; the compaction detection index $K/K_{min}$ obtained in real time is compared with a standard interval of $K/K_{min}$ in Standard Table 1 to determine the compaction status of the asphalt mixture, so as to adjust and control the construction process and construction quality in time; when a value of $K/K_{min}$ is greater than a right end value of the standard interval, a section is under-compacted and supplementary compaction construction should be implemented in time; when the value of $K/K_{min}$ is smaller than a left end value of the standard interval, the section is over-compacted and a remedial measure for over-compaction should be taken in time; when the value of $K/K_{min}$ is within the range of the standard interval, the compaction of the base course is completed and steps 1-5 may be repeated to construct the intermediate and surface courses.

Compared with the prior art, the present invention has the following advantages.

1. The present invention tests accurately and provides immediate guidance for an actual construction compaction process. The compaction detection index of the asphalt mixture is measured in real time during the construction compaction process. The compaction status of the asphalt mixture is accurately determined on site according to the compaction detection index. A smaller compaction detection index indicates a better compaction status of the asphalt mixture, and a greater compaction detection index indicates a worse compaction status of the asphalt mixture. Based on the compaction detection index obtained on site, the detection device monitors the compaction status of the mixture in real time and guides the construction on site in time. The detection device prevents and remedies under- and over-compaction conditions to ensure a good compaction effect of the asphalt mixture.

2. The present invention is simple, fast and implementable. The present invention is directly used on a construction site for construction detection to realize real-time compaction control of the asphalt mixture. In a specific implementation process, the detection device is directly transported to the construction site. The detection device tests the asphalt mixture with a certain degree of compaction during post-paving and subsequent compaction to obtain the compaction detection index of the asphalt mixture in the construction process.

3. The present invention directly tests the asphalt mixture. In a practical application, the test claw is rotated slowly and uniformly to obtain a torque to measure the compactability of the mixture in actual construction. The slow rotation protects the asphalt pavement from large damage. The shear strength and shear stiffness of the asphalt mixture obtained during compaction directly reflect the mechanical properties of the asphalt mixture during construction. In addition, the present invention can also evaluate the compaction status of the asphalt mixture according to the calculated compaction detection index.

4. The present invention has a simple and reasonable structure and a wide range of applications, and is detectable for various types of asphalt mixtures. The present invention accurately reflects a compaction viscosity resistance of the asphalt mixture through the mixing of the asphalt mixture, which is expressed in the form of a torque. Then the present invention obtains the shear strength and shear stiffness of the asphalt mixture during compaction to directly reflect the mechanical properties of the asphalt mixture during construction. On this basis, the present invention determines whether to perform timely supplementary compaction. The present invention realizes accurate and immediate detection of the compaction status of asphalt mixtures with different proportions. Therefore, the present invention has universality and can be popularized in asphalt pavement construction.

Figure 1:
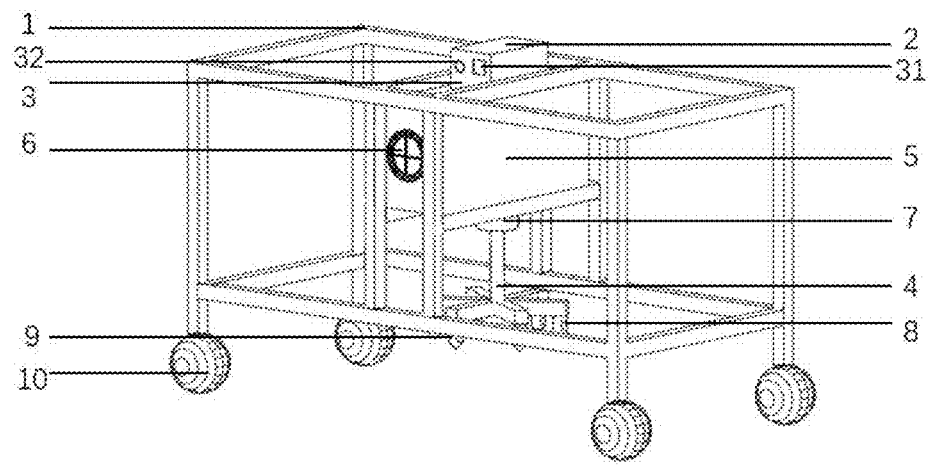
FIG. 1 is a structural diagram of a device for detecting compaction and shear strength characteristics of an asphalt mixture during construction compaction according to the present invention.

Reference numerals: 1. fixed frame; 2. display; 3. control panel; 31. power switch; 32. speed regulator; 4. test claw; 5. electric motor; 6. lift switch; 7. torque sensor; 8. temperature sensor; 9. claw blade; and 10. universal wheel.

DETAILED DESCRIPTION

To make the technical means, creative features, purpose of use and effects of the present invention comprehensible, the present invention is further described blow with reference to the specific implementations.

Figure 2:
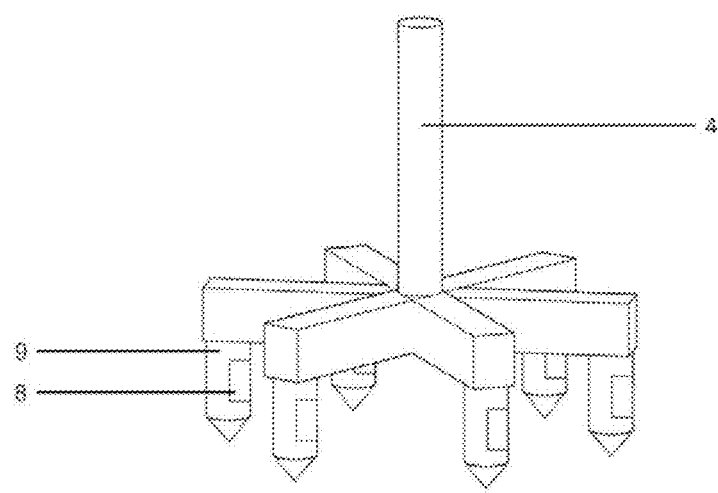
FIG. 2 is a structural diagram of a test claw.

Referring to FIG. 1 and FIG. 2, the present invention provides a preferable device for detecting compaction and shear strength characteristics of an asphalt mixture during construction compaction. The device includes a fixed frame 1 and a detection system. A universal wheel 10 is arranged at the bottom of the fixed frame 1 to facilitate a free movement for on-site construction detection. The detection system includes a display 2, a control panel 3, a test claw 4, an electric motor 5 for driving the test claw 4 to rotate, a lift switch 6 for controlling a vertical movement of the test claw 4, a torque sensor 7 and a temperature sensor 8. The control panel 3 includes a power switch 31 for controlling the electric motor 5 and a speed regulator 32 for controlling a rotation speed of the test claw 4. An output end of the electric motor 5 is connected to an input end of the torque sensor 7, and an output end of the torque sensor 7 is connected to an input end of the test claw 4. An output end of the test claw 4 is provided with a claw-shaped blade 9. There are 6 claws of the claw-shaped blade 9. The bottom of the claw-shaped blade is a conical tip, which is convenient for pressing into the asphalt mixture with a certain degree of compaction. The claw-shaped blade is provided therein with the temperature sensor 8.

Figure 3:
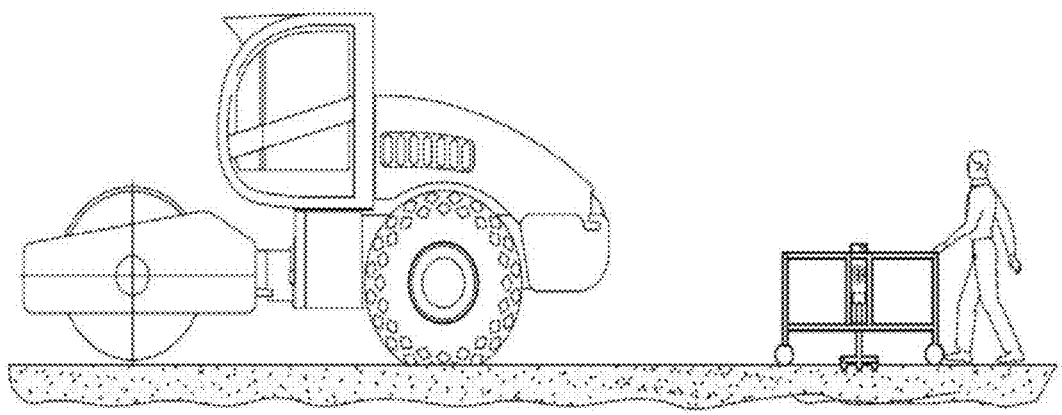
FIG. 3 is a diagram showing the use of a device for detecting compaction and shear strength characteristics of an asphalt mixture.

As shown in FIG. 3, a specific process is as follows:

step 1: surface, intermediate and base courses of the asphalt mixture are paved separately on site; after the base course is compacted by a compactor, the detection device is moved to a selected detection point, and the universal wheel is fixed;

step 2: the claw-shaped blade on the output end of the test claw is pressed into the asphalt mixture with a certain degree of compaction through a lift switch;

step 3: the power switch of the electric motor is turned on; the electric motor drives a stirring shaft to rotate slowly and uniformly with a speed freely selected between 5°/min and 10°/min; a temperature T (° C.) and a torque M (N·m) on the display are recorded;

step 4: the torque M obtained in step 3 is used to calculate a shear strength and a shear stiffness of the asphalt mixture:

$$F = G\gamma = \frac{M\rho}{I_p}$$

$$G = \frac{F}{\gamma} = \frac{M\rho}{\gamma I_p}$$

where, F is the shear strength, G is the shear stiffness, $\gamma$ is a shear strain, $\rho$ is a radius, and $I_p$ is a polar moment of inertia; and step 5: the shear strength and the shear stiffness obtained in step 4 are used to calculate a compaction detection index $K/K_{min}$ of the asphalt mixture, where K is defined as an inverse of the shear stiffness, $$K = \frac{1}{G},$$

and $K_{min}$ is a minimum value of K of the asphalt mixture under a corresponding degree of compaction; the compaction detection index $K/K_{min}$ obtained in real time is compared with a standard interval of $K/K_{min}$ in Standard Table 1 to determine the compaction status of the asphalt mixture, so as to adjust and control the construction process and construction quality in time; when a value of $K/K_{min}$ is greater than a right end value of the standard interval, a section is under-compacted and supplementary compaction construction should be implemented in time; when the value of $K/K_{min}$ is smaller than a left end value of the standard interval, the section is over-compacted, and a remedial measure for over-compaction should be taken in time; when the value of $K/K_{min}$ is within the range of the standard interval, the compaction of the base course is completed and steps 1-5 may be repeated to construct the intermediate and surface courses.

The corresponding values of the compaction detection index $K/K_{min}$ and the degree of compaction in Table 1 are standard values obtained by using the detection device and method of the present invention to repeatedly detect the design asphalt mixture (AC-13C asphalt mixture herein) and acquire and calibrate the data in a design stage. It should be noted that the values in the standard table may vary with different design asphalt mixtures in actual engineering, but the detection device and method used are essentially unchanged.

TABLE 1

Standard table of compaction detection index $K/K_{min}$ and degree of compaction in correspondence

| Degree of compaction | | 0.8 | 0.82 | 0.84 | 0.86 | 0.88 | 0.9 | 0.92 | 0.94 | 0.96 | 0.98 |
|---|---|---|---|---|---|---|---|---|---|---|---|
| $K/K_{min}$ | Left end value | 0.8 | 0.82 | 0.84 | 0.85 | 0.86 | 0.87 | 0.88 | 0.88 | 0.9 | 0.9 |
| | Right end value | 2.2 | 2.0 | 1.8 | 1.7 | 1.6 | 1.5 | 1.4 | 1.3 | 1.2 | 1.2 |

The corresponding values of the compaction detection index $K/K_{min}$ and the degree of compaction in Table 1 are standard values obtained by using the detection device and method of the Table 1 shows that the compaction detection index $K/K_{min}$ calculated by the detection device is inversely proportional to the degree of compaction. A higher degree of compaction indicates a worse compactability of the mixture and a smaller compaction detection index. Based on the compaction detection index obtained on site, the detection device monitors the compaction status of the mixture in real time and adjusts the construction in time to prevent and remedy the under- and over-compaction conditions. The compaction detection index, the degree of compaction and other volume indexes are used together for construction guidance to achieve dual control of the construction compaction index and ensure a good compaction effect of the asphalt mixture.

Embodiment 1

In this embodiment, for example, an AC-13C asphalt mixture in a surface course is under a post-paving state. Three compactors are used to compact a section with a compaction method as shown in Table 2.

TABLE 2

Compaction method of section

| Compaction step | Primary compaction | Secondary compaction | Final compaction |
|---|---|---|---|
| Type of compactor | Steel drum compactor | Vibratory compactor | Steel drum compactor |
| Compaction speed (km/h) | 3 | 4 | 5 |
| Compaction times | 2 | 2 | 3 |

The corresponding values of the compaction detection index $K/K_{min}$ and the degree of compaction in Table 1 are standard values obtained by using the detection device and method of the A compactor follows a paver to perform primary compaction. After static compaction by a steel drum compactor, a nuclear-free density gage is used to measure a degree of compaction of the asphalt mixture. Compaction and shear strength characteristics detection device is used to measure a real-time compaction detection index $K/K_{min}$ and an internal temperature T of the mixture. An electric motor drives a stirring shaft to rotate slowly and uniformly. A rotation speed is freely selected from 5°/min to 10°/min. Detection indexes of the compaction status are shown in Table 3.

TABLE 3

Detection indexes of primary compaction status of section

| Stake No. | Internal temperature of mixture °/C. | Degree of compaction/% | $K/K_{min}$ |
|---|---|---|---|
| K2 + 060 | 127.1 | 82 | 1.96 |
| K2 + 080 | 129.9 | 86 | 1.24 |
| K2 + 100 | 126.2 | 84 | 1.27 |

The corresponding values of the compaction detection index $K/K_{min}$ and the degree of compaction in Table 1 are standard values obtained by using the detection device and method of the purpose of the primary compaction is to level and stabilize the mixture, while creating a condition for secondary compaction. After the primary compaction is completed, the degree of compaction of the mixture reaches more than 80%, and the primary compaction temperature is maintained at 110-130° C., which is a normal construction temperature. Compared with compaction and shear strength characteristics index $K/K_{min}$ under a corresponding degree of compaction in FIG. 4 and a standard value in Table 1, the compaction detection index $K/K_{min}$ of the asphalt mixture in each section is in the range of a standard interval. This indicates a good primary compaction status of the mixture.

The secondary compaction follows the primary compaction. The secondary compaction is a key step for the compaction, stabilization and formation of the mixture. After the secondary compaction is completed with a vibratory compactor, the compaction performance of the asphalt mixture is detected the same as that in the primary compaction step. The detection indexes of the compaction status are shown in Table 4.

TABLE 4

Detection indexes of secondary compaction status of section

| Stake No. | Internal temperature of mixture °/C. | Degree of compaction/% | $K/K_{min}$ |
|---|---|---|---|
| K2 + 060 | 90.4 | 86 | 1.84 |
| K2 + 080 | 110.6 | 95. | 1.24 |
| K2 + 100 | 108.2 | 97 | 1.02 |

The corresponding values of the compaction detection index $K/K_{min}$ and the degree of compaction in Table 1 are standard values obtained by using the detection device and method of the For section K2+060, the degree of compaction after the secondary compaction is too small. The detection index $K/K_{min}$ of the mixture is 1.84, which is greater than a normal value of 1.70 under a corresponding degree of compaction (86%), indicating that the compaction of the section is not qualified. The internal temperature of the mixture is 90.4° C., which is lower than a normal secondary compaction temperature (95-115° C.). Therefore, remedial construction cannot be performed, and it is recommended that the section be scrapped and repaved.

For section K2+080, the temperature of the mixture is acceptable. The compaction detection index $K/K_{min}$ of the mixture is 1.24, which is greater than a normal value of 1.20 under a corresponding degree of compaction (95%). This indicates that the internal mechanical property of the mixture is not up to standard, and the compaction of the mixture is unqualified. The following methods may be used to improve the mechanical property of the mixture:

1. replace the vibratory compactor with a tire compactor to knead the mixture to reduce the friction between particles and allow a small particle to enter a gap between large particles; and 2. slow down the compaction of the vibratory compactor and increase the contact time between the compactor and the mixture; or adopt a high-frequency large-amplitude method to generate a large excitation force.

For section K2+100, the internal temperature, the degree of compaction and the compaction and shear strength characteristics of the mixture all are acceptable, indicating that the mixture is in good compaction status and a next stage of construction may be implemented.

What is claimed is:

1. A device for detecting compaction and shear strength characteristics of an asphalt mixture during construction compaction, comprising a fixed frame (1) and a detection system, wherein the detection system comprises a display (2), a control panel (3), a test claw (4), an electric motor (5) for driving the test claw (4) to rotate, a lift switch (6) for controlling a vertical movement of the test claw (4), a torque sensor (7) and a temperature sensor (8); the control panel (3) comprises a power switch (31) for controlling the electric motor (5) and a speed regulator (32) for controlling a rotation speed of the test claw (4); an output end of the electric motor (5) is connected to an input end of the torque sensor (7), and an output end of the torque sensor (7) is connected to an input end of the test claw (4); an output end of the test claw (4) is provided with a claw-shaped blade (9); the claw-shaped blade (9) is provided therein with the temperature sensor (8).

2. The device for detecting compaction and shear strength characteristics of an asphalt mixture during construction compaction according to claim 1, wherein there are at least 3 claws of the claw-shaped blade (9).

3. The device for detecting compaction and shear strength characteristics of an asphalt mixture during construction compaction according to claim 2, wherein there are 3-6 claws of the claw-shaped blade (9).

4. The device for detecting compaction and shear strength characteristics of an asphalt mixture during construction compaction according to claim 1, wherein the bottom of the claw-shaped blade is a conical tip.

5. The device for detecting compaction and shear strength characteristics of an asphalt mixture during construction compaction according to claim 2, wherein the bottom of the claw-shaped blade is a conical tip.

6. The device for detecting compaction and shear strength characteristics of an asphalt mixture during construction compaction according to claim 3, wherein the bottom of the claw-shaped blade is a conical tip.

7. The device for detecting compaction and shear strength characteristics of an asphalt mixture during construction compaction according to claim 4, wherein a universal wheel (10) is arranged at the bottom of the fixed frame (1) to facilitate a free movement.

8. The device for detecting compaction and shear strength characteristics of an asphalt mixture during construction compaction according to claim 5, wherein a universal wheel (10) is arranged at the bottom of the fixed frame (1) to facilitate a free movement.

9. The device for detecting compaction and shear strength characteristics of an asphalt mixture during construction compaction according to claim 6, wherein a universal wheel (10) is arranged at the bottom of the fixed frame (1) to facilitate a free movement.

\* \* \* \* \*